United States Patent [19]
Lee et al.

[11] Patent Number: 5,648,583
[45] Date of Patent: Jul. 15, 1997

[54] PROCESS FOR CONVERTING EXO-ISOMERS OF ALKYL SUBSTITUTED CYCLOPENTADIENES TO ENDO-ISOMERS

[75] Inventors: John Y. Lee; Meng-Sheng Ao; Stephen E. Belmont; Lawrence H. Shepherd, Jr., all of Baton Rouge, La.

[73] Assignee: Albemarle Corporation, Richmond, Va.

[21] Appl. No.: 429,448

[22] Filed: Apr. 27, 1995

[51] Int. Cl.$^6$ .................. C07C 5/25; C07C 5/23; C07C 5/00
[52] U.S. Cl. .................. 585/664; 585/601; 585/669; 585/377; 585/324; 585/23; 585/350
[58] Field of Search .................. 585/601, 664, 585/669, 377, 327, 324, 23, 350

[56] References Cited

U.S. PATENT DOCUMENTS 5,434,324  7/1995  Lee et al. .................. 585/357

FOREIGN PATENT DOCUMENTS 4009-341-A  4/1992  Japan.
2096165  10/1981  United Kingdom.

*Primary Examiner*—Glenn A. Caldarola
*Assistant Examiner*—Thuan D. Dang
*Attorney, Agent, or Firm*—Philip M. Pippenger

[57] ABSTRACT

Exo-isomers of polyalkylcyclopentadienes are converted to endo-isomers by contacting the exo-isomers with an acid such as aqueous HCl.

14 Claims, No Drawings

PROCESS FOR CONVERTING EXO-ISOMERS OF ALKYL SUBSTITUTED CYCLOPENTADIENES TO ENDO-ISOMERS

The invention relates generally to polyalkyl-substituted cyclopentadienes and more specifically to a process for converting exo-isomers of such polyalkyl-substituted cyclopentadienes to endo-isomers.

Alkyl substituted cyclopentadienes are used in forming metallocenes of transition metals. Such metallocenes are useful components of olefin polymerization catalysts as is known in the art. Polyalkyl substituted cyclopentadienes, such as 1-methyl-3-n-propylcyclopentadiene, as prepared, for example, from cyclopentenones are typically comprised of mixtures of endo- and exo-isomers. In theory there are 5 possible stable endo- and 3 possible stable exo-isomers. The structure of one isomer of each type is illustrated below for a typical 1,3-disubstituted cyclopentadiene.

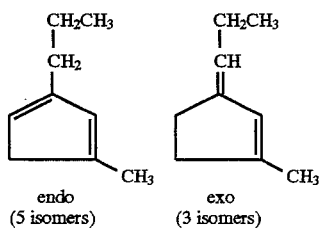

endo (5 isomers)     exo (3 isomers)

It has been found that when the mixture of endo- and exo-cyclopentadiene is reacted with a suitable deprotonating agent (such as butyl lithium) and then with a transition metal halide to form a metallocene, the exo-isomers do not react to form the metallocene and often remain unchanged in the reaction mixture. Under suitable reaction conditions the exo-isomers can be easily recovered in ≧90% purity from the product mixture by employing a suitable technique such as by vacuum distillation. Because the amount of exo-isomers can initially constitute from 25 to 50 percent or more of the isomer mixture, this represents a considerable reduction in the overall yields of metallocene product. We have now found a process for converting a significant portion of the exo-isomers to useful endo-isomers.

In accordance with this invention there is provided a process for converting exo-isomers of polyalkyl substituted cyclopentadienes to endo-isomers, said process comprising contacting said exo-isomers with an acid under conditions so as to convert at least a portion of said exo-isomers to the desired endo-isomers.

The synthesis of polyalkylcyclopentadienes, such as 1-methyl-3-alkylcyclopentadienes, by the reaction of 3-methyl-2-cyclopentene-1-one with alkyl Grignard reagents such as methyl, ethyl, n-propyl or isopropyl magnesium halides, followed by alcohol formation and dehydration using relatively strong acids such as HCl or p-toluene sulfonic acid is described in the literature. These processes give about a 50/50 mixture of endo- and exo-isomers. According to the improved process described in allowed copending application Ser. No. 08/137,683, filed Oct. 15, 1993, endo- to exo-isomer ratios of 2.5 to 1 or higher can be achieved. Because of similar boiling points, separation of these isomers is difficult. However, when the mixture is deprotonated, followed by metallation to produce the desired metallocene, the exo-isomers do not react and almost pure (≧90%) exo-isomers can be recovered by distillation. This, heretofore waste product, can then be converted to useful mixtures of exo- and endo-isomers in accordance with the process of the invention, without any significant impurities being formed by contacting the mixture with an acid. The endo-enriched mixtures of polyalkylcyclopentadienes can then be recycled to the metallation process to produce additional metallocene product.

The polyalkylcyclopentadienes which can form mixtures of endo- and exo-isomers are substituted with two or more alkyl or substituted alkyl groups having from 1 to 20 or more carbon atoms, such as 1,3-dialkyl substituted cyclo pentadienes. Included within the definition of such polyalkylcyclopentadienes are compounds in which two or more adjacent groups can join to form ring structures which can be further substituted. Non-limiting examples of the substituent groups include methyl, ethyl, propyl, isopropyl, butyl, isobutyl, tert-butyl, amyl, isoamyl, hexyl, cyclohexyl, heptyl, octyl, nonyl, decyl, and the like and groups which form a condensed ring compound with the cyclopentadienyl group such as 1,2-dimethylene-, 1,2-trimethylene-, 1,2-tetramethylene-, and the like.

The exo-isomers are contacted with an acid which is effective to convert at least a portion of the exo-isomers to endo-isomers. Inorganic acids are preferred such as HCl, $BF_3$ or $H_2SO_4$, but relatively strong organic acids such as formic acid, methanesulfonic acid, p-toluenesulfonic acid, or polymer-bonded sulfonic acid can be used. Most preferred is aqueous HCl and especially 1 to 20 wt. percent aqueous HCl which can be used in substantial excess, but is preferably used in proportions which provide about 0.1 to 10 wt. percent contained HCl relative to the weight of exo-isomers. The exo-isomers can be treated neat, but the isomerization rate appears to be faster when they are dissolved in an organic solvent such as an ether, for example, diethyl ether or tetrahydrofuran, or aliphatic and aromatic hydrocarbons and halo-hydrocarbons such as chloroform, toluene, and methylene chloride so as to form a two-phase system with the aqueous acid. The solvent can be used to provide, for example, a 10 to 50 wt. percent solution of isomers. Other means of contacting the acid and exo-isomers, such as feeding dry HCl gas to a solvent solution of exo-isomer, passing the exo-isomers in a solvent through a column containing acid supported on a solid, or mixing the acid and exo-isomers in a miscible solvent can be used. Ambient temperatures (about 20°–25° C.) in the absence of solvent produce a slow reaction rate but elevated temperatures (30° to 60° C.) provide a faster reaction such that increased conversion of exo- to endo-isomers is obtained in a few hours. A suitable temperature and acid concentration can be readily determined, depending upon the particular compound, so as to provide the maximum conversion (about a 50/50 mixture) to endo-isomers in a reasonable time without producing large amounts of side products such as tars.

The invention is further illustrated by, but is not intended to be limited to, the following examples.

EXAMPLE 1

A mixture of isomers of 1-methyl-3-n-butylcyclopentadiene (1 ml) containing about 6.6% endo-isomers, 80.8% exo-isomers, 0.6% impurities, and 12% toluene as an internal standard (values are area percent as measured by gas chromatography) or a ratio of endo/exo-isomers of 1:12.2 was mixed with 1 ml of aqueous HCl (5 wt. percent) and stirred at 22° C. Samples were analyzed by GC at the times noted in Table I below.

TABLE I

| | (GC Analysis Area %) | | | |
|---|---|---|---|---|
| Reaction Time (hrs) | Toluene | Endo-Isomers | Endo-Isomers | Impurities |
| 1 | 12.2 | 7.4 | 80.1 | 0.3 |
| 2 ½ | 11.0 | 7.8 | 80.9 | 0.3 |
| 5 | 12.1 | 8.5 | 78.9 | 0.5 |

Apparently at 22° C., the exo- to endo-isomerization is very slow.

EXAMPLE 2

The process of Example 1 was repeated at a temperature of 50°–55° C. The results are shown in Table II below. A endo/exo-isomer ratio of 1:1.1 was achieved after 11 hours.

TABLE II

| | (GC Analysis Area %) | | | |
|---|---|---|---|---|
| Reaction Time (hrs) | Toluene | Endo-Isomers | Exo-Isomers | Impurities |
| ½ | 11.4 | 13.1 | 74.5 | 1.0 |
| 2 ½ | 11.4 | 25.6 | 61.9 | 1.1 |
| 5 | 11.5 | 36.0 | 50.4 | 2.3 |
| 7 | 10.8 | 38.9 | 47.9 | 2.4 |
| 9 | 11.8 | 40.0 | 46.0 | 2.2 |
| 11 | 12.2 | 40.0 | 44.2 | 3.6 |

When a similar mixture of isomers was heated with stirring at 50° C. in the presence of diethyl ether (25 wt. % solution) using 5% wt. aqueous HCl at a pressure of 5–10 psi for about 3 hours, the endo/exo-isomer ratio as determined by GC analysis was 46:54, with a trace of impurity. This indicates that a faster reaction occurs in the presence of the ether.

Using THF/5% aqueous HCl over a period of 5 hours at 22° C., an endo/exo-isomer ratio of 38/62 (35%/58% normalized GC area %) is obtained with a small amount (7% normalized GC area %) of impurity. The use of THF, therefore, appears to speed the isomerization but can result in increased by-product formation.

EXAMPLE 3a

When anhydrous HCl (1.0M in Et$_2$O amounts of from 0.10 gram to 0.50 gram) were added to 0.50 gram of a similar mixture of exo-/endo-isomers used in Example 1 at 22° C.; both isomerization and oligomerization were fast. Therefore, the amount of HCl was reduced to 0.025 gram. The results obtained using this amount of HCl are listed in Table III.

TABLE III

| | (GC Analysis Area %) | | | | |
|---|---|---|---|---|---|
| Run Time (Hrs.) | Et$_2$O | Toluene | Endo-Isomers | Exo-Isomers | Impurities |
| 0 | 0 | 13.6 | 6.1 | 79.8 | 0.5 |
| ½ | 0.9 | 12.8 | 10.4 | 74.9 | 1.0 |
| ½ | 1.0 | 12.6 | 12.4 | 72.6 | 1.4 |
| 2 | 0.8 | 12.7 | 26.2 | 58.4 | 1.9 |
| 8 | 0.8 | 11.9 | 33.4 | 50.1 | 3.8 |
| 11 | 0.8 | 13.7 | 32.9 | 48.1 | 4.5 |

EXAMPLE 3b

Et$_2$O (1.18 grams) was added to the mixture of exo-/endo-isomers (0.50 gram) and anhydrous HCl (1.0M in Et$_2$O, 0.025 gram) at 22° C. The results are listed in Table IV. Apparently Et$_2$O speeds up the isomerization with less formation of by-products.

TABLE IV

| | (GC Analysis Area %) | | | | |
|---|---|---|---|---|---|
| Run Time (Hrs.) | Et$_2$O | Toluene | Endo-Isomers | Exo-Isomers | Impurities |
| 0 | 34.2 | 8.1 | 4.1 | 53.1 | 0.5 |
| 1 | 34.6 | 9.0 | 19.7 | 34.0 | 2.7 |
| 2 | 32.2 | 9.0 | 22.6 | 34.8 | 1.4 |
| 5 | 37.5 | 8.4 | 22.5 | 29.6 | 2.0 |
| 7 | 33.9 | 9.0 | 23.8 | 30.6 | 2.7 |

EXAMPLE 4

A mixture of 0.50 gram of the endo- and exo-isomers as per Example 3, 1.18 grams of Et$_2$O and 0.10 gram of formic acid was heated at 50° C. for 2 hrs. to produce an endo/exo-isomer ratio of 17/33 (30 area % to 58 area %) and 12 Area % oligomers (Normalized GC area %). The isomerization and by-product formation were both found to be very slow at 5° to 22° C. (5 hrs. at 5° C. and ½ hr. at 22° C.). When the mixture was heated at 50° C., both isomerization and oligomerization proceeded rapidly.

EXAMPLE 5

A strongly acidic ion-exchange resin (Amberlyst-15®) 0.033 gram was added to a mixture of 0.33 gram of isomers similar to the isomer mixture used in Example 1 and 0.67 gram of Et$_2$O at 22° C. with stirring for 5 minutes to 40 minutes. It was found that the exo-isomer oligomerized rapidly under above conditions. The isomerization was slow. It appears that a less acidic resin is needed for use in a continuous process, which would operate by passing the solution of isomer through a column packed with a solid acidic catalyst.

What is claimed is:

1. A process for converting exo-isomers of polyalkylsubstituted cyclopentadienes to endo-isomers, said process comprising contacting said exo-isomers with an acid under conditions so as to convert at least a portion of said exo-isomers to endo-isomers.

2. The process according to claim 1 wherein said acid is HCl.

3. The process according to claim 2 wherein said acid is aqueous HCl and wherein conversion of at least a portion of said exo-isomers to endo-isomers is performed at a temperature of at least about 40° C.

4. The process according to claim 3 wherein an organic solvent is present.

5. The process according to claim 4 wherein said solvent is diethyl ether.

6. The process according to claim 1 wherein conversion of at least a portion of said exo-isomers to endo-isomers is performed at a temperature of from about 20° to 60° C.

7. The process according to claim 1 wherein an organic solvent is present.

8. The process according to claim 7 wherein said organic solvent is selected from the group consisting of diethyl ether, tetrahydrofuran and mixtures thereof.

9. The process according to claim 1 wherein said polyalkyl substituted cyclopentadiene is a 1,3-dialkyl-substituted cyclopentadiene wherein the alkyl groups substituted in the 1- and 3-positions each have from 1 to 20 carbon atoms.

10. The process according to claim 7 wherein an organic solvent solution of said exo-isomers is passed through a column packed with a solid acidic catalyst.

11. The process according to claim 1 wherein said acid is anhydrous HCl.

12. The process according to claim 9 wherein said 1,3-dialkyl-substituted cyclopentadiene is a 1-methyl-3-alkylcyclopentadiene.

13. The process according to claim 11 wherein an ether solvent is present.

14. The process according to claim 13 wherein the ether is diethyl ether.

* * * * *